United States Patent
Zaage et al.

(10) Patent No.: US 9,528,823 B2
(45) Date of Patent: Dec. 27, 2016

(54) METHOD AND DEVICE FOR MEASURING THE POSITION OF SEGMENTS WITH ABSORBING SUBSTANCES IN MULTI-SEGMENT FILTER RODS OF THE TOBACCO PROCESSING INDUSTRY

(71) Applicant: TEWS Elektronik GmbH & Co. KG, Hamburg (DE)

(72) Inventors: Stefan Zaage, Hannover (DE); Udo Schlemm, Hamburg (DE); Rainer Herrmann, Hamburg (DE); Harald Ceslik, Hamburg (DE); Jörn Eggers, Quickborn (DE)

(73) Assignee: TEWS Elektronik GmbH & Co. KG, Hamburg (DE)

( * ) Notice: Subject to any disclaimer, the term of this patent is extended or adjusted under 35 U.S.C. 154(b) by 268 days.

(21) Appl. No.: 13/723,697

(22) Filed: Dec. 21, 2012

(65) Prior Publication Data

US 2014/0043045 A1 Feb. 13, 2014

(30) Foreign Application Priority Data

Dec. 22, 2011 (DE) .................... 10 2011 121 918

(51) Int. Cl.
*G01B 15/00* (2006.01)
*A24D 3/02* (2006.01)
(Continued)

(52) U.S. Cl.
CPC ............ *G01B 15/00* (2013.01); *A24C 5/3412* (2013.01); *A24D 3/0295* (2013.01); *G01N 22/04* (2013.01)

(58) Field of Classification Search
CPC ........ A24D 3/0295; G01N 22/04; G01B 15/00
(Continued)

(56) References Cited

U.S. PATENT DOCUMENTS 3,357,320 A    12/1967 Sexstone et al.
3,531,558 A *   9/1970 Ganz ............................ 264/122
(Continued)

FOREIGN PATENT DOCUMENTS

CN    202548071 U    11/2012
DE       2343668       3/1975
(Continued)

OTHER PUBLICATIONS

Ebbe Nyfors and Pertti Vainikainen: "Industrial Microwave Sensors", Industrial Microwave Sensors, (Jan. 1, 1989), XP002334964.
(Continued)

*Primary Examiner* — Jeff Natalini
(74) *Attorney, Agent, or Firm* — Vidas, Arrett & Steinkraus, P.A.

(57) ABSTRACT

A method and device for measuring the position of sections with an absorbing substance in multi-segment filter rods of the tobacco processing industry by measuring a varying shift of the resonance frequency A and/or spread of the resonance line B during movement of the rod in the longitudinal direction, using a microwave resonator, which has a field concentration in a spatial area, wherein this spatial area is smaller in the rod direction than the segment length to be determined, forming a difference quotient ΔA of the resonant frequency shift A and/or ΔB of the resonance line spread B relative to the longitudinal direction, determining local extreme values of the respective difference quotients, and assigning local extreme values as a position of a transition from a section with higher content of absorbing substance to a section without, or with lower content, of absorbing substance, and vice versa.

16 Claims, 2 Drawing Sheets

(51) Int. Cl.
  *G01N 22/04* (2006.01)
  *A24C 5/34* (2006.01)
(58) Field of Classification Search
  USPC .......................................................... 324/635
  See application file for complete search history.

(56) References Cited

U.S. PATENT DOCUMENTS

| | | | |
|---|---|---|---|
| 5,977,780 A * | 11/1999 | Herrmann | 324/640 |
| 6,062,226 A * | 5/2000 | Kida | 131/84.1 |
| 6,075,882 A | 6/2000 | Mullins et al. | |
| 7,132,836 B2 * | 11/2006 | Peters et al. | 324/637 |
| 7,439,722 B2 | 10/2008 | Poulet et al. | |
| 7,580,137 B2 | 8/2009 | Wilson et al. | |
| 7,911,212 B2 * | 3/2011 | Herrmann et al. | 324/637 |
| 8,330,473 B2 | 12/2012 | Herrmann et al. | |
| 2005/0096202 A1 * | 5/2005 | Teufel et al. | 493/39 |
| 2007/0091326 A1 | 4/2007 | Schroeder et al. | |
| 2008/0054912 A1 * | 3/2008 | Herrmann et al. | 324/640 |
| 2011/0125047 A1 * | 5/2011 | Scheib | 600/544 |
| 2013/0036793 A1 * | 2/2013 | White et al. | 73/24.02 |

FOREIGN PATENT DOCUMENTS

| | | |
|---|---|---|
| DE | 2455271 | 5/1976 |
| DE | 10159233 A1 | 6/2003 |
| DE | 10146953 B4 | 10/2007 |
| EP | 0235023 A1 | 9/1987 |
| EP | 0902277 | 3/1999 |
| EP | 1197746 | 4/2002 |
| EP | 1327876 A1 | 7/2003 |
| WO | 2008/075032 A1 | 6/2008 |

OTHER PUBLICATIONS

"Radio Spectrum", (Jan. 1, 2015), XP055180254, URL:http://ptolerny.eecs.berkeley.edu/eecs20/sidebars/radio/ (found on Mar. 30, 2015).
Dimitrios Ventzas et al.., "Peak Searching Algorithms and Applications", Signal and Image Processing and Applications/716: Artificial Intelligence and Soft Coomputing, (Jan. 1, 2011), XP055180273, Calgary, AB, Canada.
Bahl, I.J., Chapter "1 Introduction" on p. 1. Lumped elements for RF and microwave circuits, 2003.
Dumpala, et al., "An algorithm for the detection of peaks in biological signals", Computer Programs in Biomedicine 14 (Jun. 1, 1982) 249-256, Elsevier Biomedical Press.
Jarman et al., "A new approach to automated peak detection", Chemometrics and Intelligent Laboratory Systems 69 (Nov. 28, 2003) pp. 61-76.
Paul Voglewede: "Parabola Approximation for Peak Determination", Global DSP, (May 1, 2004), XP055180274, URL:http://www.ingelec.uns.edu.ar/pds2803/Materiales/Articulos/AnalisisFrecuencial/GlobalDSPMay2004.pdf.
Knut Martin Morken: "Chapter II Numerical Differentiation and Integration", (Jan. 1, 2008), pp. 227-269, XP055180277, URL:http://www.uio.no/studier/emner/matnat/math/MAT-INF1100/h08/kompendiet/diffint.pdf.
CH Townes et al.: "Microwave Spectroscopy", (Jan. 1, 1975), Dover Publications, XP055180610.
AD McCormack et al.: "A Comparison of Granular Additives for use in Cigarette Filters", (Jan. 1, 2005), pp. 1-4, XP055180528, URL:http://www.essentrafilters.com/media/14705/2005-A-Comparison-of-Granular-Additives-for-Usein-Cigarette-Pdf-.pdf (found on Mar. 31, 2015).

* cited by examiner

METHOD AND DEVICE FOR MEASURING THE POSITION OF SEGMENTS WITH ABSORBING SUBSTANCES IN MULTI-SEGMENT FILTER RODS OF THE TOBACCO PROCESSING INDUSTRY

CROSS-REFERENCE TO RELATED APPLICATIONS

This Utility Application claims priority to DE 2011 121 918.1 filed on Dec. 22, 2011.

STATEMENT REGARDING FEDERALLY SPONSORED RESEARCH

Not applicable.

BACKGROUND OF THE INVENTION

The present invention relates to a method and a device for measuring the position of segments with one or more absorbing substances in multi-segment filter rods of the tobacco processing industry.

In order to make the filter effect of cigarette filters composed of cellulose acetate filters more effective and more selective, granulates of finely dispersed particles of absorbing material are often added to cellulose acetate filters. Active charcoal granulates are an example which due to a large inner pore surface absorb primarily unpolarized molecules from the tobacco smoke. Also included for this purpose, are other materials in powder form, such as finely dispersed tobacco, silica gel, or wood shavings that are incorporated into the cigarette filter. The granulate is introduced in a filter rod maker as a process step into the outspread cellulose acetate, before the arrival thereof for spraying of a plasticizer for forming the endless filter rod, which is then enclosed with paper and cut into individual rods. In a multi-segment filter rod maker, individual segments of differently doped filter rods are joined together, including pure cellulose acetate rods such that ultimately a finished filter element for a cigarette results from two or more segments.

Here, the concentration of the granulate is not uniformly distributed in the filter tow. The concentration depends both on the uniformity of the application as well as the uniformity of the subsequent compression of the filter tow into the filter rod during rod formation in the inlet funnel of the filter rod maker. The degree of compression depends on the ratio of the speed of the arriving, outspread filter tow to the speed of the endless filter rod. Consequently, it is of great interest to detect both the distribution of the granulate in the individual segments of the endless filter rod as well as the individual positions of the segment edges as a profile measurement, and to exclude imperfect filter rods from the production. A filter rod is imperfect then if the average value of granulate deviates too much from a predetermined target value, the distribution in the filter rod is too non-homogeneous, or the measured positions of the segment edges do not conform with the target values for the segment edges.

From the document DE 101 59 233 A1, the entire contents of which is incorporated herein by reference, a method is known for producing filters for filter cigarettes. With the method, a filter granulate is applied in cycles before the endless rod shaping device such that zones with granulate and without granulate, preferably of uniform length, alternate with each other in the endless filter rod. The transition from the zones without granulate to zones with granulate is detected using a microwave resonator. With the known method, both the shift of the resonance frequency and the spread of the resonance curve are detected and evaluated. Due to the volume expansion of the measurement region in the microwave resonator, the spatial resolution of the known method is too poor in order to detect the transition edge.

BRIEF SUMMARY OF THE INVENTION

An object of the invention is to provide a method and a device of the initially named type that allows an exact spatial resolution and thus precise detection of the segment edges, by the simplest means possible.

The method according to the invention is provided and intended for measuring the position of sections with an absorbing substance in multi-segment filter rods of the tobacco processing industry. Absorbing substances are understood in the following to mean substances which due to their good absorption properties, are capable of filtering out specific molecules or molecule groups from tobacco smoke. As in the case of active charcoal, the substances can also be electrically conductive. With the method according to the invention, a temporally varying shift of the resonance frequency A and/or spread of the resonance lines B during movement of a filter rod in the longitudinal direction thereof is measured using a microwave resonator. Here, the microwave resonator has a field expansion that is smaller in the direction of the endless filter rod than the length of a filter segment to be measured. The microwave resonator measures in a known manner the shift of the resonance frequency A thereof with respect to the empty state thereof, and/or an enlargement of the full width at half maximum of the resonance curve B. In a subsequent step, a difference quotient $\Delta A$ and/or $\Delta B$ of the resonance frequency shifts and resonance curve spreads is formed with respect to the longitudinal direction of the filter rod. The difference quotient specifies at a location, or in a location range, how the resonance frequency shift and/or resonance curve spread changes with the location.

With the method according to the invention, the local extreme values are determined from the respective difference quotients. Thus, with the evaluation of the resonance frequency shift, a local extreme value of $\Delta A$ is determined in the longitudinal direction of the filter rod. Correspondingly, with the evaluation of the resonance curve spread, a local extreme value of $\Delta B$ is determined in the longitudinal direction of the endless filter rod. The extreme values are the local maximums and local minimums. According to the invention, in the next step the local extreme values are assigned as a position of a transition from one section with a higher content of absorbing substances to a section without absorbing substances, or with a lower content of absorbing substances, and vice versa. The invention is based on the recognition that the position of the transition to a section with an absorbing substance can be precisely determined by the maximums and minimums of the respective difference quotients, because the change of the A value, or B value, of the resonator is the greatest when the segment edge of the endless multi-filter rod passes directly through the maximum of the electric field of the microwave resonator that is spatially very narrowly limited. The method according to the invention permits a resolution of the position of the transition that is significantly less than the spatial resolution, thus the field concentrations zone, of the microwave resonator that is used.

In a preferred further development of the method according to the invention, a predetermined minimum length is provided for a filter segment to be measured. This minimum length of a filter segment preferably must not be less than the spatial extension of the electrical field of the resonator in the direction of the endless rod because otherwise it is no longer possible to determine the position of the segment edge. Thus, it is advantageous to design the resolution range of the resonator to be as small as possible. The minimum length for the size of the filter segments serves for the purpose of detecting the local extreme values along the longitudinal direction of the filter rod, or respectively if required in order to switch from detection of maximum of the difference quotients to detection of minimums as a consequence of a change of sign of the difference quotients. For this purpose, the local extreme values are determined as absolute extreme values on the minimum length. If the minimum length is greater than the expected distance between the two sections to be recorded, and is less than double the distance, then an absolute extreme value on the minimum length corresponds to a local extreme value.

Alternatively or additionally, it is also possible to determine the local extreme values of the difference quotient in that maximum values, or respectively minimum values, are predetermined and upon falling below or exceeding of which, a subsequent extreme value is identified as a local extreme value of the difference quotient. Also, falling below the predetermined minimum value can be used as an indication that there must have been a previous local maximum, and subsequently a local minimum is to be detected. Likewise, upon exceeding the predetermined maximum value, wherein then a local minimum must have previously been present, a local maximum follows.

In a further preferred design, a transition from a region with an absorbing substance to a region without an absorbing substance is assigned to a minimum of the difference quotient. Correspondingly, it is preferred to assign a transition from a region without an absorbing substance to a region with an absorbing substance to a maximum of the difference quotient. A transition from a region of lower density of the absorbing material to a region of greater density generally corresponds to a maximum of the difference quotient, that can be measured precisely at the transition edge of the two segments. Conversely, a transition from a region of higher density of the absorbing material to a region of lower density, generally corresponds to a minimum of the difference quotient, that occurs again exactly at the transition edge of the two segments. In focusing on the maximum values, or respectively the minimum values of the difference quotient, the inflection points in the shift of the resonance frequency A, or respectively the spread of the resonance curve B, can be precisely identified. The dielectric properties of the measured filter rods change in the inflection points due to the absorbing substances, such that the transition, and thus the segment edge, can be detected very precisely. Thus, this relates not only to segment edges between one segment of the filter tow material having an absorbing substance, but rather also to edges between segments with different absorbing substances, and to edges between segments with different densities of the same absorbing substance.

In a further improvement of the spatial resolution, a predetermined curve, the peak value of which is determined as a position of the transition, is fitted to the measurement values around the extreme value of the difference quotient. In that a predetermined curve, preferably a parabola, is fitted, for example by regression, to difference quotients around the extreme value and the vicinity thereof, the position of the extreme value of the difference quotient can be determined very precisely from great number of measurement values in the vicinity of the extreme value.

In a preferred further development of the method according to the invention, additionally the mass of the absorbing substance in a segment is determined, wherein the mass value is determined proportionally to the progression of A values and/or B values integrated in the longitudinal direction between the two segment edges. Because the boundaries of the section are known very precisely using the method according to the invention, a reproducible and precise measurement value can preferably be obtained by integrating A values and/or the B values between two adjacent segment edges. This integrated value between two adjacent segment edges is caused by the absorbing substance in the section, and thus is proportional to the total mass of absorbing substance present in the section.

Preferably, active charcoal is introduced by sections in an endless filter rod as an absorbing substance. The proportion of the measured shifts in resonance frequency, which is caused by fluctuations of the density in the filter tow, is low with respect to the shift of the resonance frequency, which is caused by the active charcoal.

In another case, silica gel is preferably introduced by sections into an endless filter rod as an absorbing substance. The proportion of the measured spread of the resonance curve, which is caused by fluctuations of the density in the filter tow, is low with respect to the spread of the resonance curve, which is caused by the silica gel granulate.

The device according to the invention is provided and intended for measuring the position of segments with absorbing substances in multi-segment filter rods of the tobacco processing industry. The device has a microwave resonator, the electric field lines of which are concentrated in a measurement zone that is smaller in the transport direction of the endless filter rod than the smallest size of a segment of the endless filter rod. In addition, the device has a measurement device for detecting a varying resonance frequency shift A and/or a resonance line spread B with respect to the values of the empty resonator during movement of the multi-segment filter rod in the longitudinal direction thereof through the measurement zone of the microwave resonator. Thus, using the measurement device, a profile in the longitudinal direction of the filter rod is recorded regarding the resonance frequency shift A and/or the resonance line spread B. Furthermore, the device according to the invention is provided with an evaluation unit for determining the difference quotient ΔA of the resonance frequency shift A and/or the difference quotient ΔB of the resonance line spread to the longitudinal direction of the multi-segment rod. The evaluation unit is further provided to determine local extreme values of the respective difference quotients and to assign the determined local extreme values as a position of the respective segment edges. The device according to the invention with its evaluation unit permits a very exact determination of segment edges, thus the position of the segments in the multi-segment filter rod can be determined very precisely.

The measurement zone in the microwave resonator in the direction of the endless rod is preferably less than 10 mm if the segment length to be determined is greater than or equal to the 10 mm. If the segment lengths to be determined are greater than or equal to 3 mm, processing can be performed with a measurement zone that is less than 3 mm in the endless rod direction.

In a particularly preferred design, the microwave resonator is disposed in a multi-segment filter maker. In such a maker, the endless filter rod is moved forward using a drive of the maker. The position of the endless filter rod, which must be known for example for forming the difference quotient, is preferably acquired in this design by digital pulsed signals of the multi-segment filter maker. Thus, in this design a microwave resonator is integrated in a multi-segment filter maker, wherein the evaluation unit obtains the position signals thereof from one or more drives of the multi-segment filter maker.

Also, it is possible to dispose the microwave resonator in a filter rod test station, in which the filter rod is driven by a step motor. In this design, the position of the endless filter rod performing the difference quotient is measured using signals from a step motor of the filter rod test station.

BRIEF DESCRIPTION OF THE SEVERAL VIEWS OF THE DRAWINGS

The invention is explained in the following in more detail using an example embodiment. In the figures.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
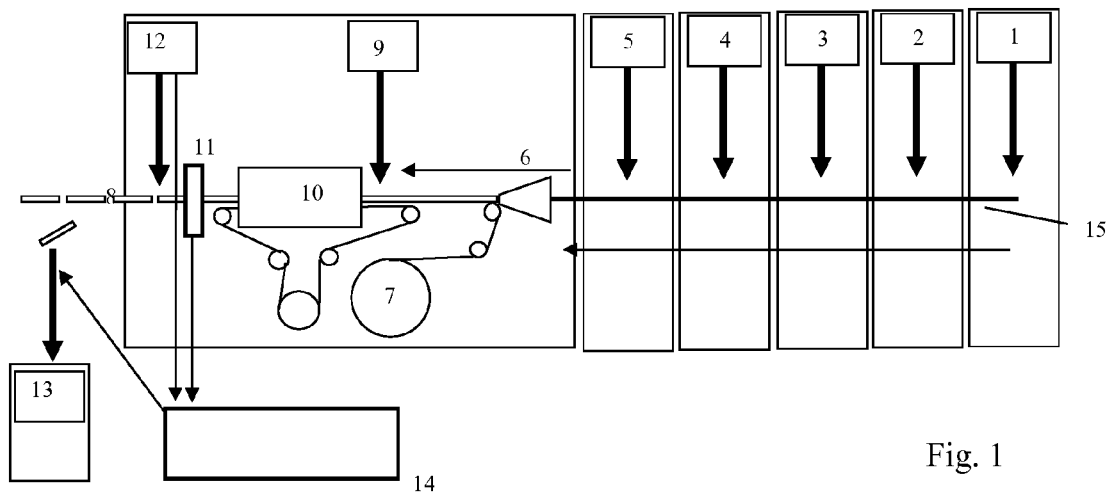
FIG. 1 shows a filter rod maker with a microwave sensor at the endless filter rod for the position measurement of the granulate.

FIG. 1 shows a schematic view of a multi-filter rod maker with a microwave resonator 11 at the endless multi-filter rod for measuring the position and determining the content of the segments. A transport device 15 passes through a row of supply stations 1 to 5. In the supply stations, individual segments can be admitted continuously in non-stop operation, or clocked, to the transport device 15. A section-wise supply of active charcoal segments, for example, occurs in such a supply station.

The thusly prepared endless multi-filter rod is transported in the direction T, and passes through an inlet funnel 6, in which the endless multi-filter rod is formed. Paper is supplied to the endless multi-filter rod from a paper bobbin 7. Glue supply occurs in the dispensing station 9, wherein the glue hardens in a heating zone 10. An endless filter rod enclosed with paper emerges from the heating zone and passes through the microwave resonator 11. In the microwave resonator 11, a resonance frequency shift A, or respectively resonance spread B of the resonance curve is measured with respect to the empty microwave resonator, and the measured values are further supplied to a microwave measurement unit 14. The measurement unit 14 evaluates, according to the method according to the invention, the position of the sections with the absorbing substance, such as active charcoal, and controls an ejection unit 13, with which imperfect filter rods are ejected. The endless filter rod measured in the microwave resonator 11, is cut into filter rods 16 using a clocked-operating cutting device 12. With the filter rod maker according to FIG. 1, the microwave resonator is disposed after the heating zone 10, and thus functions online in the multi-filter rod maker. Alternatively or additionally, it is also possible to provide a microwave resonator 11 that functions at-line in a control unit and on which multi-segment filter rods are measured on a sample basis.

Figure 2:
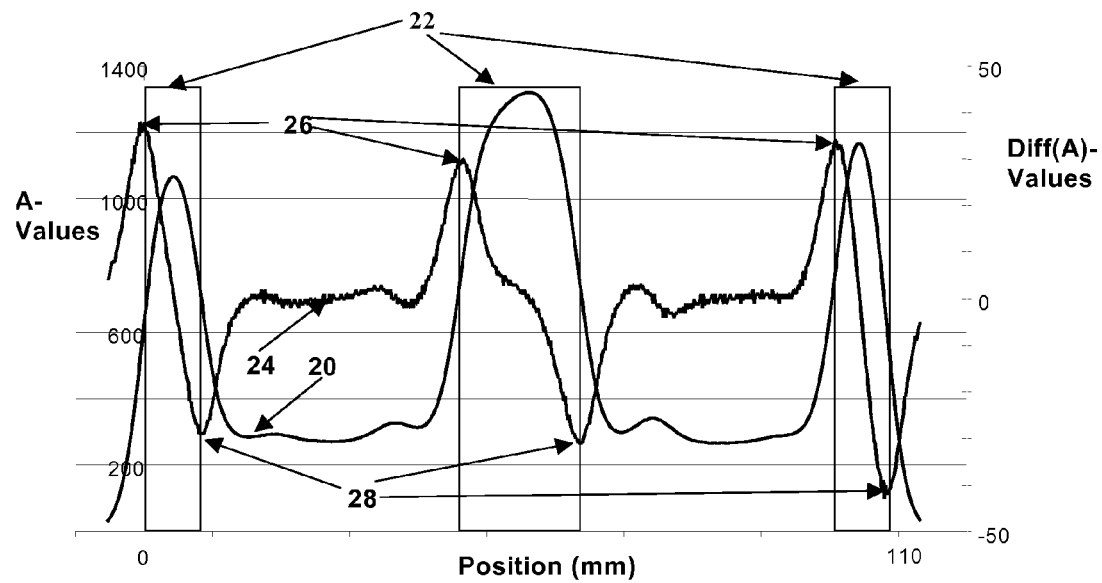
FIG. 2 shows example measurement values for the resonance frequency shift at a filter rod.

FIG. 2 shows the progression of the resonance frequency shift A in an endless filter rod over a length of approximately 110 mm. In the range between 0 mm and 10 mm, 45 mm and 65 mm and 100 mm to 110 mm, active charcoal is introduced in the gray shaded regions 22. It can be clearly seen in FIG. 2 that the measured values 20 recorded for the resonance frequency shift A respectively have a maximum in the sections 22. At the same time, it can also be seen that the measured values already increase before the sections 22, and also decrease slowly following the sections 22.

This occurs because the measurement field of the microwave resonator 11 has a spatial resolution of approximately 3 mm. In FIG. 2, the difference quotients of the A values are marked with 24. The difference quotient $\Delta A$ is calculated as follows:

$$\Delta A = \frac{A(X1) - A(X2)}{X1 - X2},$$

where $A(X1)$, $A(X2)$ designate the measured resonance frequency shift A at the positions X1 and X2. Other definitions of the difference quotient are possible with two or more grid points. The progression 24 of the $\Delta A$ values determined as a difference quotient respectively shows in FIG. 2 a maximum 26 at the transition from a region without active charcoal into a region with active charcoal, and a minimum 28 at the transition out of the region with active charcoal into a region without active charcoal.

Depending on the absorbing substance to be measured in a segment zone, the variable A (resonance frequency shift) or the variable B (resonance curve spread) of the microwave resonator can be used for determining edges and measuring content. The corresponding difference quotient of the B values is calculated analogously to the equation above:

$$\Delta B = \frac{B(X1) - B(X2)}{X1 - X2}.$$

Figure 3:
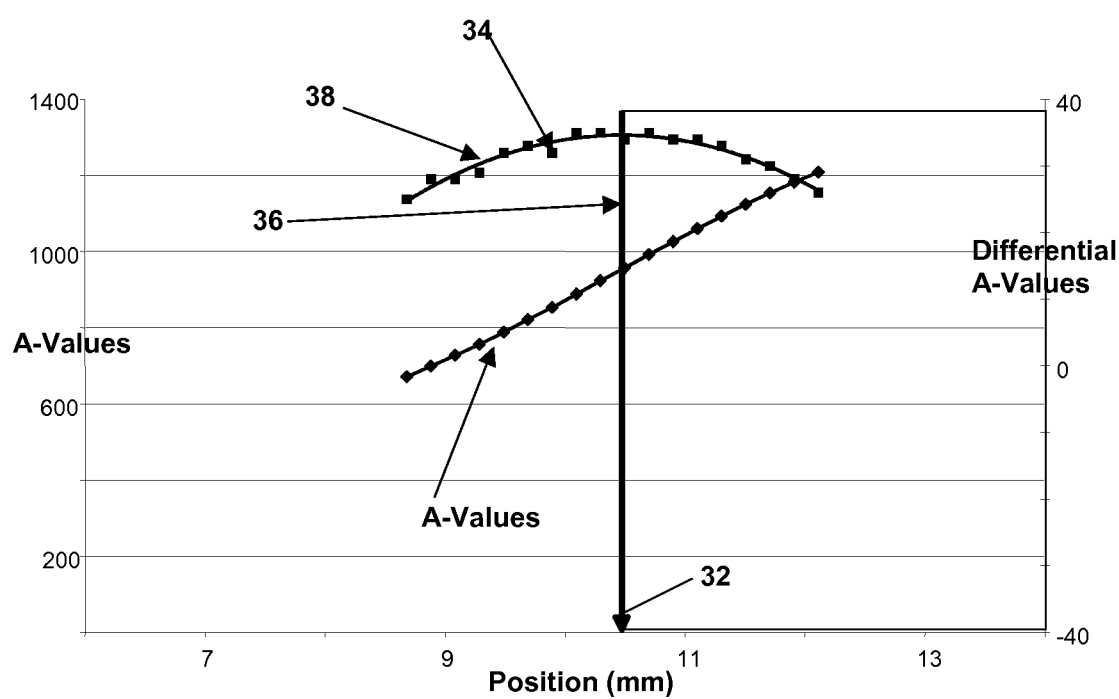
FIG. 3 shows the fitting using a parabola for determining the transition at a section with inserted active charcoal.

FIG. 3 shows in an enlarged view, a segment edge at 10.5 mm, which shows a transition from a region without active charcoal (less than 10.5 mm) into a region with active charcoal (greater than 10.5 mm) FIG. 3 is not an enlargement of the measured values from FIG. 2, but rather another example measurement at an endless filter rod. It can be seen clearly in FIG. 3, that the resonance frequency shifts 30 increase at the segment edge 32. The difference quotients 34 have a significantly more clearly structured contour which has a maximum 36 at the segment edge 32. By focusing on the maximum as an extreme value, the position of the transition can be detected more precisely.

The maximum 36 is determined in that a parabola 38 is fitted to the values for the difference quotients, for example using regression. In this manner it is possible, while determining the segment edges 32, to attain a measurement accuracy of 0.2 mm or less from a measurement signal of a microwave resonator with a field concentration zone of 3 mm in length.

Along with the measurement of the positions of the segment edges described above, the A values, or respectively B values, can also be used to determine the mass of the absorbing substance, for instance active charcoal, in the respective endless filter rod segment. By integrating the A values or the B values over the length of the respective segment, an integrated value is determined in the respective segment. Tests have shown that for active charcoal the integrated resonance frequency shift here is independent of the size of the granulate and the different types of inserted active charcoal. Although the dependency of the integral resonance frequency shift is not always linear with respect to the mass of the active charcoal per segment, this relationship that is mostly independent of type and particle size, can be determined ahead of time in a one-time calibration measurement and retained in a characteristic curve. A recalibration is not necessary between different production steps at the maker.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for measuring the position of sections having absorbing substances in a multi-segment filter rod of the tobacco processing industry, comprising the steps of:
   measuring a varying resonance frequency shift A and/or resonance line spread B during movement of the multi-segment filter rod in the longitudinal direction thereof using a microwave resonator, said microwave resonator having a field concentration in a spatial area, wherein this microwave resonator spatial area in the direction of the multi-segment filter rod is smaller than a multi-segment filter length,
   calculating a difference quotient ΔA of the resonance frequency shift A and/ or ΔB of the resonance line spread B, relative to the longitudinal direction,
   determining local extreme values of the respective difference quotients, and
   assigning the local extreme values as a position of a transition from a section with a higher content of absorbing substance to a section without absorbing substances, or with a lower content of absorbing substances, and vice versa, wherein difference quotient ΔA is calculated in accordance with the following formula $$\Delta A = \frac{A(X1) - A(X2)}{X1 - X2},$$

wherein A(X1) and A (X2) designate the measured resonance frequency shift A at the positions X1 and X2, and wherein difference quotient ΔB is calculated in accordance with the following formula $$\Delta B = \frac{B(X1) - B(X2)}{X1 - X2}.$$

wherein B(X1) and B (X2) designate the measured resonance line spread B at the positions X1 and X2.

2. The method according to claim 1, wherein a predetermined minimum length of the individual filter rod segments is provided, and the local extreme values of the difference quotient are determined as absolute extreme values on the minimum length.

3. The method according to claim 1, wherein upon falling below a predetermined minimum value of the difference quotient and/or after exceeding a predetermined maximum value, a subsequent extreme value is identified as a local extreme value.

4. The method according to claim 1, wherein a transition from a region without, or with lower content of absorbing substance, to a region with higher content of absorbing substance is assigned to a maximum.

5. The method according to claim 1, wherein a transition from one region with higher content of absorbing substance to a region without, or with lower content, of absorbing substance is assigned to a minimum.

6. The method according to claim 1, wherein a predetermined curve of difference quotients around the local extreme value is used to identify a peak value wherein said peak value is assigned as the position of transition.

7. The method according to claim 6, wherein regression analysis of the values of the difference quotients is used to define a parabola around the extreme value.

8. The method according to claim 1, wherein, the mass of the absorbing substances in a multi-segment filter is determined, and wherein the mass is proportional to the integrated A values and/or B values between two adjacent multi-segment filters.

9. The method according to claim 1, wherein active charcoal is provided in sections in the filter rod as an absorbing substance.

10. The method according to claim 1, wherein silica gel is provided in sections in the filter rod as an absorbing substance.

11. The method according to claim 1, further comprising:
    determining the mass of the absorbing substances in a multi-segment filter, wherein the mass is not proportional to the integrated A values and/or B values between two adjacent multi-segment filters;
    determining, via a calibration measurement retained in a characteristic curve, a nonlinear relationship between the mass of the absorbing substances and the integrated A values and/or B values between two adjacent multi-segment filters.

12. A device for measuring the position of segments with absorbing substances in multi-segment filter rods of the tobacco processing industry, comprising:
    a microwave resonator, the electric field lines of which are concentrated in a measurement zone that is smaller in the direction of the multi-segment filter rod than the smallest size of a segment of the multi-segment filter rod,
    a measurement device for detecting a varying resonance frequency shift A and/or a resonance line spread B with respect to the values of the empty resonator during movement of the multi-segment filter rod in the longitudinal direction thereof through the measurement zone of the microwave resonator,
    an evaluation unit for determining the difference quotient ΔA of the resonance frequency shift A and/or ΔB of the resonance line spread B, with respect to the longitudinal direction, and for determining local extreme values of the respective difference quotients, and assigning the local extreme values as a position of the respective multi-segment filter edges, wherein difference quotient ΔA is calculated in accordance with the following formula $$\Delta A = \frac{A(X1) - A(X2)}{X1 - X2},$$

wherein A(X1) and A (X2) designate the measured resonance frequency shift A at the positions X1 and X2, and wherein difference quotient ΔB is calculated in accordance with the following formula $$\Delta B = \frac{B(X1) - B(X2)}{X1 - X2},$$

wherein B(X1) and B (X2) designate the measured resonance line spread B at the positions X1 and X2.

13. The device according to claim 12, wherein the measurement zone in the microwave resonator in the direction of the multi-segment filter rod is less than 10 mm if the segment lengths to be determined are greater than or equal to 10 mm.

14. The device according to claim 12, wherein the length of the measurement zone in the microwave resonator in the direction of the multi-segment filter rod is less than 3 mm if the segment lengths to be determined are greater than or equal to 3 mm.

15. The device according to claim 12, wherein the microwave resonator is disposed in a multi-segment filter maker and the multi-segment filter rod is driven by the maker, wherein the position of the multi-segment filter rod is measured, using signals of the multi-segment filter maker, for forming the difference quotients.

16. The device according to claim 12, wherein the microwave resonator is disposed in a filter rod test station, and the multi-segment filter rod is driven by a step motor, wherein the position of the multi-segment filter rod can be measured, using signals from a step motor of the filter rod test station, for forming the difference quotients.

* * * * *